United States Patent [19]

Zawilinski

[11] Patent Number: 5,676,138
[45] Date of Patent: Oct. 14, 1997

[54] EMOTIONAL RESPONSE ANALYZER SYSTEM WITH MULTIMEDIA DISPLAY

[76] Inventor: Kenneth Michael Zawilinski, 7800 Kincheon Ct., Austin, Tex. 78749

[21] Appl. No.: 616,634

[22] Filed: Mar. 15, 1996

[51] Int. Cl.$^6$ .......................................................... A61B 5/00
[52] U.S. Cl. .............................................. 128/630; 128/905
[58] Field of Search ....................................... 128/630, 905

[56] References Cited

U.S. PATENT DOCUMENTS

| | | |
|---|---|---|
| 2,535,249 | 12/1950 | Wilhelm et al. |
| 3,034,500 | 5/1962 | Backster, Jr. |
| 3,548,806 | 12/1970 | Fisher |
| 3,727,604 | 4/1973 | Sidwell et al. |
| 4,041,617 | 8/1977 | Hollander |
| 4,331,160 | 5/1982 | Zito, Sr. |
| 4,543,957 | 10/1985 | Friedman et al. ........................ 128/630 |
| 4,683,891 | 8/1987 | Cornellier et al. |
| 4,931,934 | 6/1990 | Snyder |
| 5,110,200 | 5/1992 | Snook |
| 5,219,322 | 6/1993 | Weathers |
| 5,596,994 | 1/1997 | Bro ............................................ 128/905 |

FOREIGN PATENT DOCUMENTS

WO 90/05970  5/1990  WIPO.

*Primary Examiner*—William E. Kamm
*Attorney, Agent, or Firm*—Richard C. Litman

[57] ABSTRACT

A multimedia computerized system for detecting emotional responses of human beings and the changes therein over time. The system includes a stimulus presentation device for presenting a stimulus, such as a television commercial, occurring over a predetermined period of time to each of one or more individuals forming a population sample; measuring devices for measuring and recording a plurality of values associated with each of a plurality of physiological variables, such as heartrate, electromyography and electrodermal activity, each associated with one or more individuals; software programmed for receiving and translating each value measured by statistical calculation into a unitless statistical measure known as a z-score, then graphing the z-score on an interaction index, and then associating automatically the z-score with a semantic descriptor for an associated emotion or state of feeling, more particularly, ; and, an interactive multimedia computer for electronically storing, displaying and retrieving information and capable of at least visually displaying one or more stimuli presented at a given time interval, at least one semantic descriptor associated with the stimulus presented, and an interaction index associated with the semantic descriptor associated with the stimulus presented.

15 Claims, 9 Drawing Sheets

ANALYSIS: MOST FREQUENT QUADRANT
GROUP RESPONSE MATRIX

| VERTICAL | HORIZONTAL | | | | | | | | | | | | | | | | | | | | | | | | |
|---|---|---|---|---|---|---|---|---|---|---|---|---|---|---|---|---|---|---|---|---|---|---|---|---|---|
| HEARTRATE | EMG | 2 | 2 | 3 | 2 | 1 | 3 | 1 | 4 | 2 | 2 | 2 | 3 | 4 | 2 | 1 | 2 | 2 | 1 | 2 | 2 | 3 | 2 | 1 | 2 | 1 | 2 | 4 | 2 | 3 |
| EDA | EMG | 3 | 4 | 2 | 2 | 2 | 1 | 2 | 4 | 2 | 2 | 2 | 3 | 4 | 3 | 1 | 2 | 4 | 2 | 1 | 1 | 4 | 3 | 1 | 1 | 4 | 2 | 1 | 2 | 1 | 3 |
| EDA | HEARTRATE | 1 | 4 | 2 | 2 | 2 | 2 | 3 | 2 | 1 | 1 | 4 | 3 | 3 | 1 | 1 | 4 | 2 | 2 | 2 | 4 | 2 | 4 | 1 | 1 | 1 | 1 | 2 | 4 | 2 |
| OBSERVATION NO. | | 1 | 2 | 3 | 4 | 5 | 6 | 7 | 8 | 9 | * | 1 | 2 | 3 | 4 | 5 | 6 | 7 | 8 | 9 | * | 1 | 2 | 3 | 4 | 5 | 6 |

Fig. 8

ANALYSIS: SIGNIFICANT QUADRANTS
CHI SQUARE SIGNIFICANCE

| VERTICAL | HORIZONTAL | | | | | | | | | | | | | | | | | | | | | | | | |
|---|---|---|---|---|---|---|---|---|---|---|---|---|---|---|---|---|---|---|---|---|---|---|---|---|---|
| HEARTRATE | EMG | * | * | * | * | * | * | * | * | * | * | * | * | * | * | * | H | * | * | * | * | * | * | * | * | * | * | * | * | * |
| EDA | EMG | * | * | * | * | S | * | * | * | * | * | * | * | * | * | * | * | H | * | * | * | * | * | * | * | * | * | * | * | * |
| EDA | HEARTRATE | * | * | * | * | * | * | * | * | * | * | H | * | * | * | * | * | * | * | * | * | * | * | * | * | * | * | * | * | * |
| OBSERVATION NO. | | 1 | 2 | 3 | 4 | 5 | 6 | 7 | 8 | 9 | * | 1 | 2 | 3 | 4 | 5 | 6 | 7 | 8 | 9 | * | 1 | 2 | 3 | 4 | 5 | 6 |

EMOTIONAL RESPONSE ANALYZER SYSTEM WITH MULTIMEDIA DISPLAY

BACKGROUND OF THE INVENTION

1. Field of the Invention

The present invention relates to an apparatus for use in the field of research regarding emotional responses of human beings, more particularly, a system including measurement devices of physiological variables operably connected to a computerized analyzer and having a multimedia display for displaying resulting data, such as each of a plurality of semantic descriptors associated with each of a plurality of emotional responses of a human at a given moment over a preselected time period during the presentation of a stimulus.

2. Description of the Prior Art

As the study of clinical psychology advances, the tools used to analyze emotional responses to various stimuli presented to a subject likewise advance. Physiological variables have been traditionally used to measure changes in emotions, typically employing devices to measure galvanic skin response (GSR), blood pressure, heart rate, respiration, as well as, electromyography (EMG) and electrocardiography (EKG). The prior art reveals a wide range of applications using such typical monitoring devices, their application in large part depending upon the underlying research goal the inventor or researcher was trying to achieve while measuring one or more physiological variables.

For example, a first group of devices was developed when the field of response analysis was in its infancy. For example, U.S. Pat. No. 2,535,249 issued Dec. 26, 1950 to Wilhelm et al. describes an electric psychometer comprising simple circuitry including a Wheatstone bridge and electrodes for testing skin conductivity or resistance. A small progressive step was then taken to combine individual reactions into a group; U.S. Pat. No. 3,034,500 issued May 15, 1962 to Backster, Jr. describes an apparatus for measuring group reactions by measuring the skin conductivity of each of a plurality of individuals with a plurality of electrodes operably connected using a Wheatstone circuit to a plurality of recording arms and a chart. More recently, a galvanometrically based method has been described in U.S. Pat. No. 4,331,160 issued May 25, 1982 to Zito, Sr., which method measures variations in galvanic skin response using a pair of electrodes or polygraph in which the output device is periodically "zeroed" during interrogation of the subject.

As the technology progressed out of its infancy, the focus appeared to shift from single, simple conductivity measurements to collecting data based upon a group of physiological variables. For example, U.S. Pat. No. 3,548,806 issued Dec. 22, 1970 to Fisher describes a system for measuring changes in physiological phenomena of a group of people as they undergo emotional stress. Individually collected data of blood pressure, respiration, and galvanic skin response are processed by a signal processor and sent to a summation means to provide indications of the collective changes of the group. Such attempts yielded singular, averaged data points at any given time and changes between such points were left to the researcher to interpret.

Attempts to advance the field by progressing from measuring simple groups of physiological variables to measuring changes in the levels of each of the variables also became popular. U.S. Pat. No. 3,727,604 issued Apr. 17, 1973 to Sidwell et al. describes an interactive emotional level indicating system in which galvanic skin response is amplified by either negative-rate or positive-rate amplifiers to activate one of two light signals to provide immediate feedback whether emotional levels are increasing or decreasing. Whereas the '604 patent describes a device which indicated a linear scale (positive-negative, increasing-decreasing) for a single variable, U.S. Pat. No. 4,041,617 issued Aug. 16, 1977 to Hollander describes a device to simulate a plurality of emotional ranges simulating a decision making process wherein multiple polar scales are employed sensitive to subjectively entered input. One or more emotional levels are thus metered having magnitudes and polarity (for such emotions as Like-Dislike, Feelings: Bad-Good, Guilt-Pride) based on decisional influences (such as Personal Desire, Social Expectations, etc.) having physical force analogs (such as the adjustment of dials and switches attached to a potentiometer). These dials cause forces of variable magnitudes to be transduced, which forces are then compared by a comparing means with the plurality of other set forces to drive a decision indicator. Conflicting decisional influences can reveal polarized readings on the meters.

However, such a device summarizing data subjectively interpreted by the subject for input, or, crude on-off light systems, exemplifies the failure in the state of the art to be able to take a physiological measurement which could then be translated into visually or graphically represented data for analysis or feedback. The need for a cognitive mediation step by a subject to interpret an emotional response to a stimulus defeats the goal of obtaining objective data points for interpretation and limits the ability to provide immediate real time feedback on a second to second basis with suddenly changing stimuli. Thus, a need exists to tie immediate analysis of emotional response to the collection of one or more physiological variables.

As personal computing power advances, the ability to stimulate a subject over incrementally smaller time intervals and display real time feedback likewise increases. U.S. Pat. No. 4,683,891 issued Aug. 4, 1987 to Cornellier et al. describes a device to implement a method to calculate and modify an individual's stress point during performance of a goal-oriented cognitive task. Physiological variables of a subject are monitored during play of a video game; difficulty of play is increased until productivity is decreased at which point biofeedback stimuli are visually presented on the video screen to assist the subject in reducing the stress level, whereupon play is resumed and the cycle repeated. However, the '891 invention is directed at providing biofeedback to a subject regarding a stress level at a threshold moment in time and is not directed at displaying cognitive information or data regarding changes in a plurality of emotional responses over a set of time points.

Another method and system utilizing a computer with a keyboard and peripheral drawing device is described in U.S. Pat. No. 4,931,934 issued Jun. 5, 1990 to Snyder. A subject first inputs locations and intensities of physical sensations felt by the subject, e.g. aches and pains; then, inputs subjective responses to a chosen focus, e.g. free associating a phrase with a given word, by drawing a subconsciously projected line; then inputs a word describing an emotion associated with a given point on the line and consciously gives an intensity rating to each such word; then further free associates on the subsequent words and so on; and finally graphs on a ± scale the intensity of emotion as it is perceived to change over time.

A three dimensional graph is further presented composed of emotion vectors plotted by the system on three axes representing a positive-negative, it-me, and active-passive differentiation of emotions and data so collected is intended for statistical analysis for predicting reaction to a given stimulus. Although a simple polar scale and tri-axial plot is described in the '934 patent, the critical drawback is that each of the input functions is subjective and performed by the subject; the system is incapable of using output based on anything other than the subjective data of the above described inputs.

Other patents of general interest to response analysis to a stimulus but less relevant to the present invention are described in the prior art. U.S. Pat. No. 5,219,322 issued Jun. 15, 1993 to Weathers describes a psychotherapy apparatus and method for treatment of undesirable emotional arousal of a patient through the coordinated and controlled presentation of alternating and changing visual stimuli between the extremes of visual range and auditory stimuli to each ear of a stationarily-positioned patient. World Intellectual Property Organization publication No. 90/05970 published May 31, 1990 by Dewey et al. describes a computerized system for expert data collection and analysis including an optical reader which collects data from a previously completed data collection form to make a recommendation based upon the responses read.

None of the above inventions and patents, taken either singly or in combination, is seen to describe the instant invention as claimed.

SUMMARY OF THE INVENTION

The present invention relates to an apparatus for use in the field of research regarding emotional responses of human beings, more particularly, a system including measurement devices of physiological variables operably connected to a computerized analyzer and having a multimedia display for displaying resulting data, such as each of a plurality of semantic descriptors associated with each of a plurality of emotional responses of a human at a given moment over a preselected time period during the presentation of a stimulus.

A multimedia computerized system is described for measuring, analyzing, storing and displaying emotional responses elicited by one or more human beings being or having been presented a stimulus. The system comprises a stimulus presentation device for presenting a stimulus, such as a television commercial, occurring over a predetermined period of time to each of one or more individuals forming a population sample; measuring devices for measuring and recording a plurality of values associated with each of a plurality of physiological variables, such as heartrate, electromyography (EMG) and electrodermal activity (EDA), each associated with one or more individuals; software programmed for receiving and translating each value measured by statistical calculation into a unitless statistical measure known as a z-score, then graphing the z-score on an interaction index, and then associating automatically the z-score with a semantic descriptor for an associated emotion or state of feeling; and, interactive multimedia computing means for electronically storing, displaying and retrieving information and capable of at least visually displaying one or more stimuli presented at a given time interval, at least one semantic descriptor associated with the stimulus presented, and an interaction index associated with the semantic descriptor associated with the stimulus presented.

The software program or translation means includes a statistical and graphics program run on a computer processing means having a memory on which the software program is installed and operationally linked to the measuring means and programmed to receive the measured output value as input for the program. The program is further capable of at least generating a plurality of interaction indices, each index comprising two axes and four quadrants defined by the two axes, and each quadrant being labelled by quadrant indicia. Each axis is labelled by an indicia associated with a different one of a pair of said plurality of the physiological variable measurements and all possible pair combinations of the physiological variables are represented among the group of interaction indices provided. For example, three interaction indices are provided when EMG, heartrate, and EDA are measured, resulting in interaction indices having axes labelled, EMG and heartrate, EMG and EDA, and EDA and heartrate.

The program further provides that plurality of sectors are superimposed on the area comprising each interaction index wherein a semantic descriptor identifies a basic state of human feeling labels each said sector. Such sectors can be further subdivided into bands associated with the intensity of each of the human feelings. Such labelling is based upon accepted theory of emotional response. For example, EMG, electrical activity in muscles measured (e.g. muscles involved in positive and negative facial expressions such as smiles, laughter, and frowns) has been associated with a dimension called Pleasure. Thus, an axis associated with EMG can be labelled by the bipolar adjectives, pleasure-displeasure. Each dimension is superimposed on each associated axis thus creating such interaction indices as Arousal (Heartrate)-Pleasure (EMG), Dominance (EDA)-Arousal (Heartrate), and Dominance(EDA)-Pleasure(EMG). Within the quadrants defined by the axes associated with these dimensions the sectors are delineated and labelled accordingly.

The program is further capable of plotting at least one of each z-score generated from the input value onto an interaction index and places an associated time-interval-identifying indicia on a plotted z-score, whereby a labelled trajectory across each interaction index is created. Furthermore, a semantic descriptor is automatically applied to each z-score falling on a sector of each interaction index. Each of these results can then be graphically displayed and stored by the interactive multimedia computing means for later retrieval.

In a second embodiment, an eye movement detection device can be added and correlated to the program to provide additional information to specifically pinpoint the viewing area seen by the subject at the moment in time that the emotional response is elicited by the stimulus.

Accordingly, it is a principal object of the invention to provide a means by which to detect a human emotional response at a moment in time in response to stimulus presented at that moment in time.

It is another object of the invention to provide means by which an emotional response can be detected by directly measuring an associated physiological variable.

It is a further object of the invention to provide means by which an emotional response can be semantically described automatically upon detection.

Still another object of the invention is to provide means by which the intensity of an emotional response can be semantically described automatically upon detection.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention relates to an apparatus for use in the field of research regarding emotional responses of human beings, more particularly, a system including measurement devices of physiological variables operably connected to a computerized analyzer and having a multimedia display for displaying resulting data, such as each of a plurality of semantic descriptors associated with each of a plurality of emotional responses of a human at a given moment over a preselected time period during the presentation of a stimulus.

As a matter of background, the present invention operates on two theories of emotion, each of which are based on the premise that one or more physiological responses, such as electrical muscle activity, precede the identification of an emotional response in reaction by an individual to a stimulus.

The present invention comprises (1) a stimulus presentation device for presenting a stimulus occurring over a predetermined period of time to each of one or more individuals forming a population sample, measuring devices to measure a change in each of a plurality of physiological variables, (2) translation or processing means, namely a software program installed on a computerized processing means, to translate each value of a physiological variable for each individual into a common unitless measure of emotional response at any one preselected unit of time over a preselected period of time and to apply automatically a semantic descriptor to each common unitless measure of emotional response falling on a sector of an interaction index, and (3) an interactive multimedia computer for electronically storing, displaying and retrieving information and capable of at least visually displaying at least one stimulus presented at any given time interval, at least one semantic descriptor associated with the stimulus presented, and an interaction index associated with the semantic descriptor associated with the stimulus presented.

Figure 1:
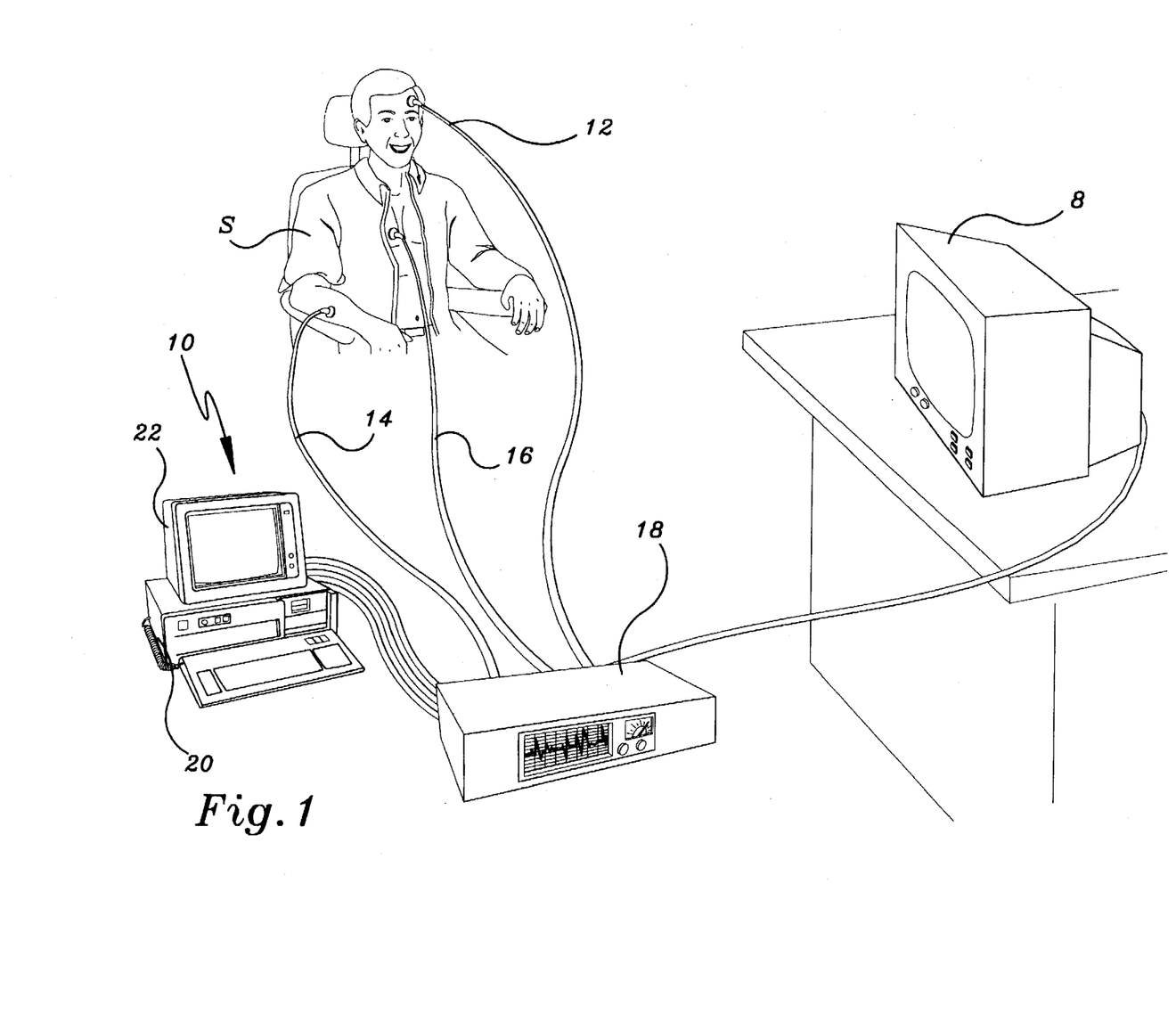
FIG. 1 is an diagrammatic view of the present invention and its representative component parts in use.

Referring first to FIG. 1, the preferred embodiment of the present invention 10 is shown wherein an individual or subject S is being monitored for emotional response while being presented a visual, verbal and non-verbal stimulus by a television monitor 8. Any population of individuals forming a sample may be chosen and prescreened according to any demographic, geographic, psychographic, product use, or other criteria of interest. As shown in FIG. 1, each individual may be attached to an electrode on the head 12, an electrode on the hand 14 and an electrode on the chest 16. These electrodes represent any sensory device known in the prior art for measuring a physiological variable. For example, numerous devices are known which can be used to monitor electromyographic activity (EMG), heartrate, electrodermal activity (EDA) including galvanic skin response (GSR), skin conductance response (SCR), and skin potential response (SPR). The preferred embodiment 10 utilizes at least three of such measuring devices for measurement of a value associated with each of the three associated physiological variables measured at any one moment in time during presentation of the stimulus. The measuring devices 12,14,16, for purposes of description, represent a sensory device each monitoring EMG, heartrate, and EDA, respectively.

Each such measuring device 12,14,16 may be combined into a single system 18; one such suggested measurement system is the Neurodata Physiograph Research Systems I-410. Data obtained through such system may be recorded using Neurodata Software (Version 2.0)) used in conjunction with a computer processing unit 20. Authorware Professional™ multimedia software and a multimedia display monitor 22 may be used in conjunction with computer processing unit 20 to display the data obtained.

Figure 2:
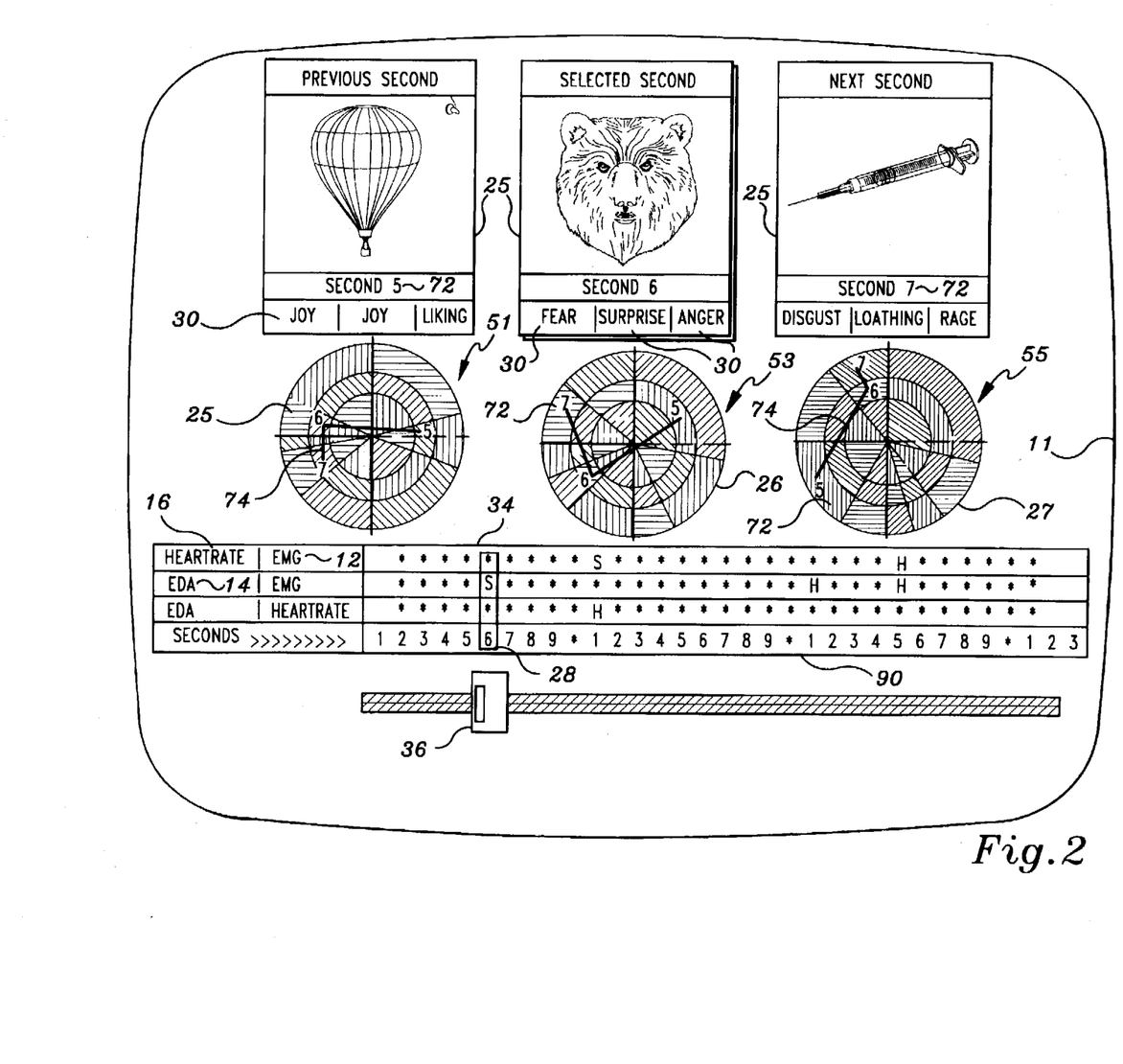
FIG. 2 is a diagrammatic view of a representative screen generated by the present invention as shown on a computer monitor.

Referring now to FIG. 2, a representative screen 11 of the data obtained is shown as displayed by the preferred embodiment 10 for presentation of the emotional response data as gathered and processed by the present invention. Each of three final interaction indices, 51,53,55 associated with a selected time interval 28 and presentation of a stimulus 25 at such time interval is shown. The selected time interval 28 also corresponds to a semantic descriptor 30 obtained by processing the value obtained from the measuring devices 12,14,16 for the selected time interval. A matrix 34 of statistical significance calculated by a statistical software program based on the input of the values of the physiological variables measured at the selected time interval is also shown. Finally, a scroll bar 36 is provided for interactive use by a user of the system to retrieve and display any one interval of time to see the emotional response data for that moment.

The gathering and processing of the emotional response data generally by the preferred embodiment is first described in reference to each of the component parts of the present invention as shown in FIG. 1. An individual S of a sample is exposed to a stimulus presentation device, e.g. a television commercial shown on a television monitor 8. In order to obtain an emotional response correctly corresponding to each of a recorded time continuum, the physiological variable value recorded, and the stimulus 25 shown at an instant during such recorded time continuum, the start of stimulus may be coded with a signal to start the measuring devices, as suggested by the wire connection 6. Thus, the measuring devices 12,14,16 record each physiological variable value at a moment in time which can be coordinated with time sequence of the stimulus 25 presented. As each value is gathered, translation means record and translate each value of the physiological variable for each individual measured into a common unitless measure of emotional response at any one preselected unit of time over a preselected period of time.

In the preferred embodiment, a statistical software program installed on computer processing unit 20 is operationally linked to measuring devices 12,14,16 such that, as each value is received for each physiological variable, the value is converted. The statistical program calculates a z-score expressed in units of the standard deviations from the mean of a distribution probability for the sample for each physiological variable measured at a given time point. The z-score, being an undefined unit, allows comparison between variables having different units of measurement, such as found among EMG, EDA, and heartrate.

Figure 3:
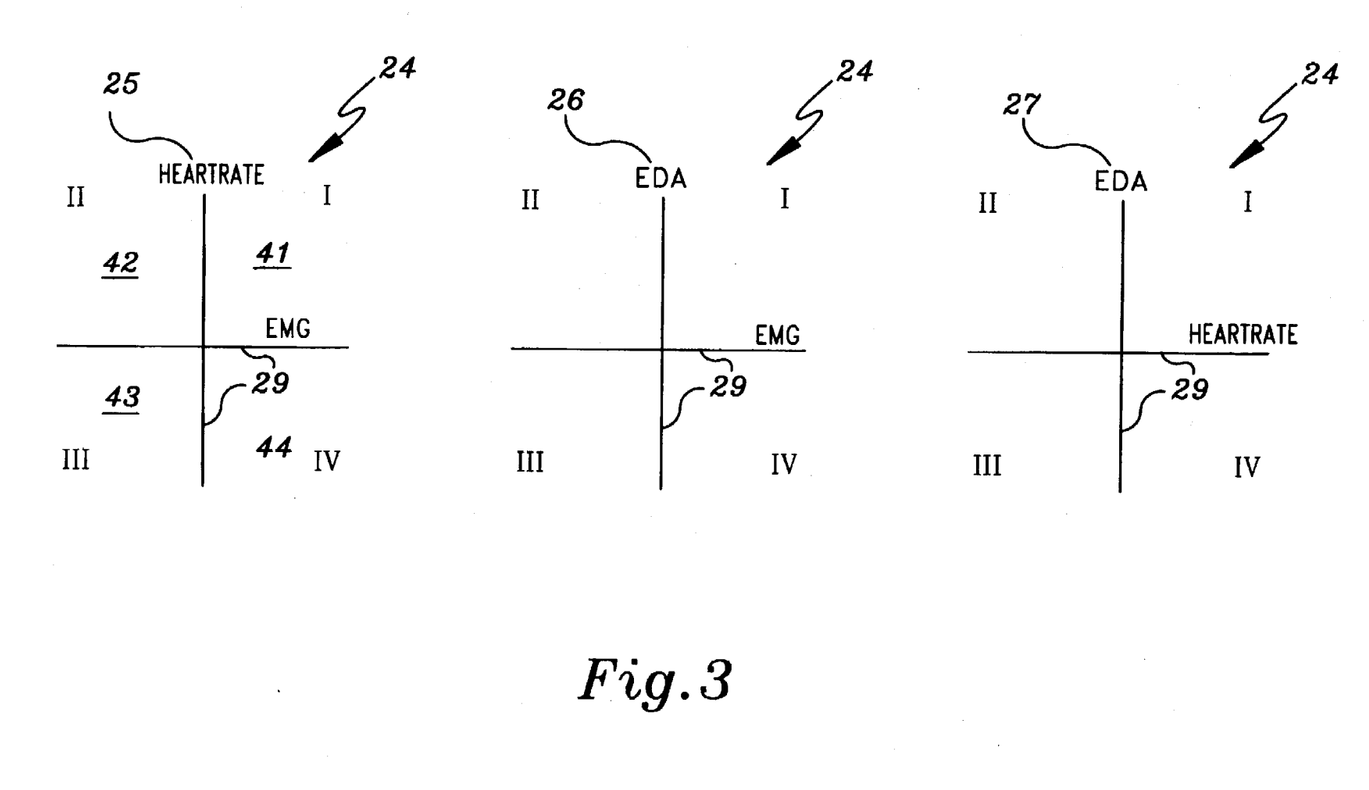
FIG. 3 is a diagrammatic representation of an interaction index.
Figure 4:
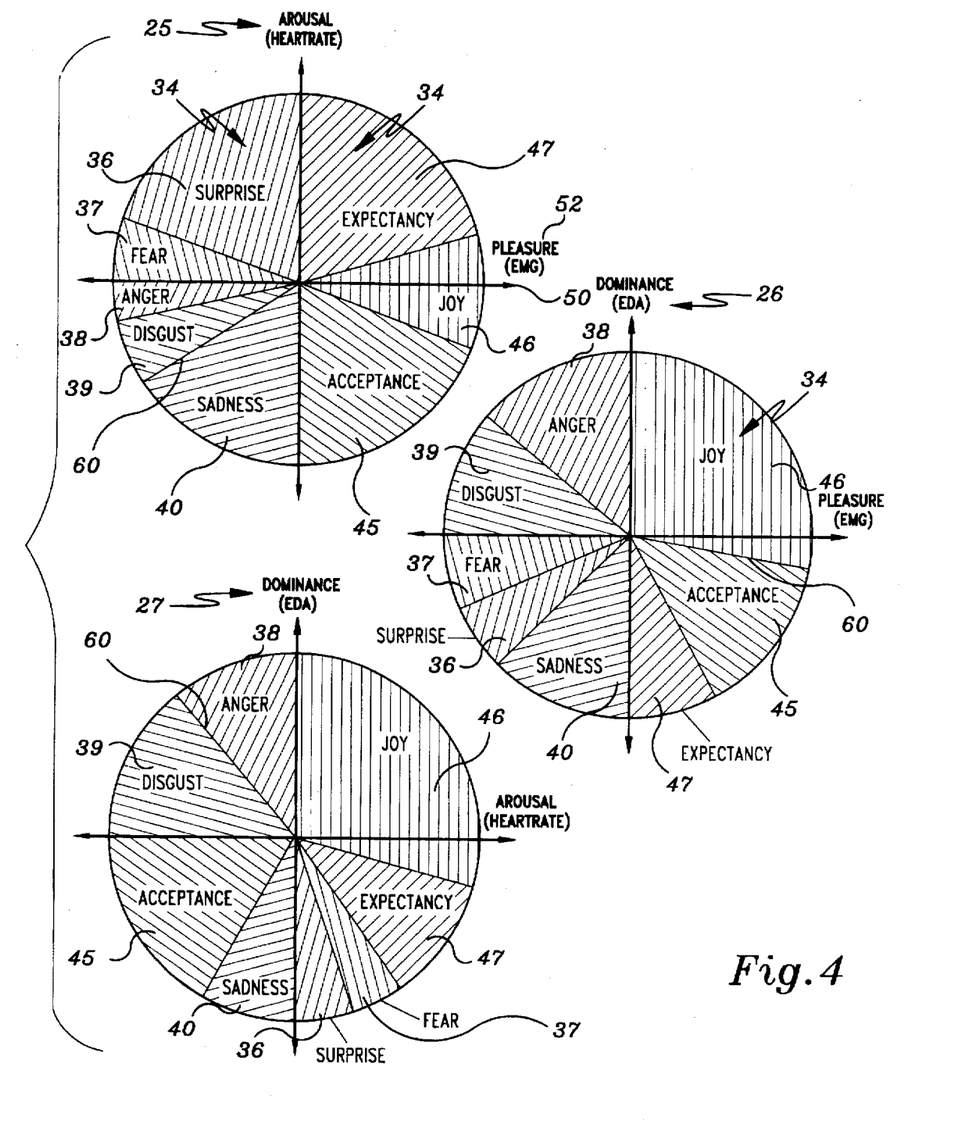
FIG. 4 is a diagrammatic representation of an interaction index having sectors labelled with semantic descriptors of emotion.
Figure 5:
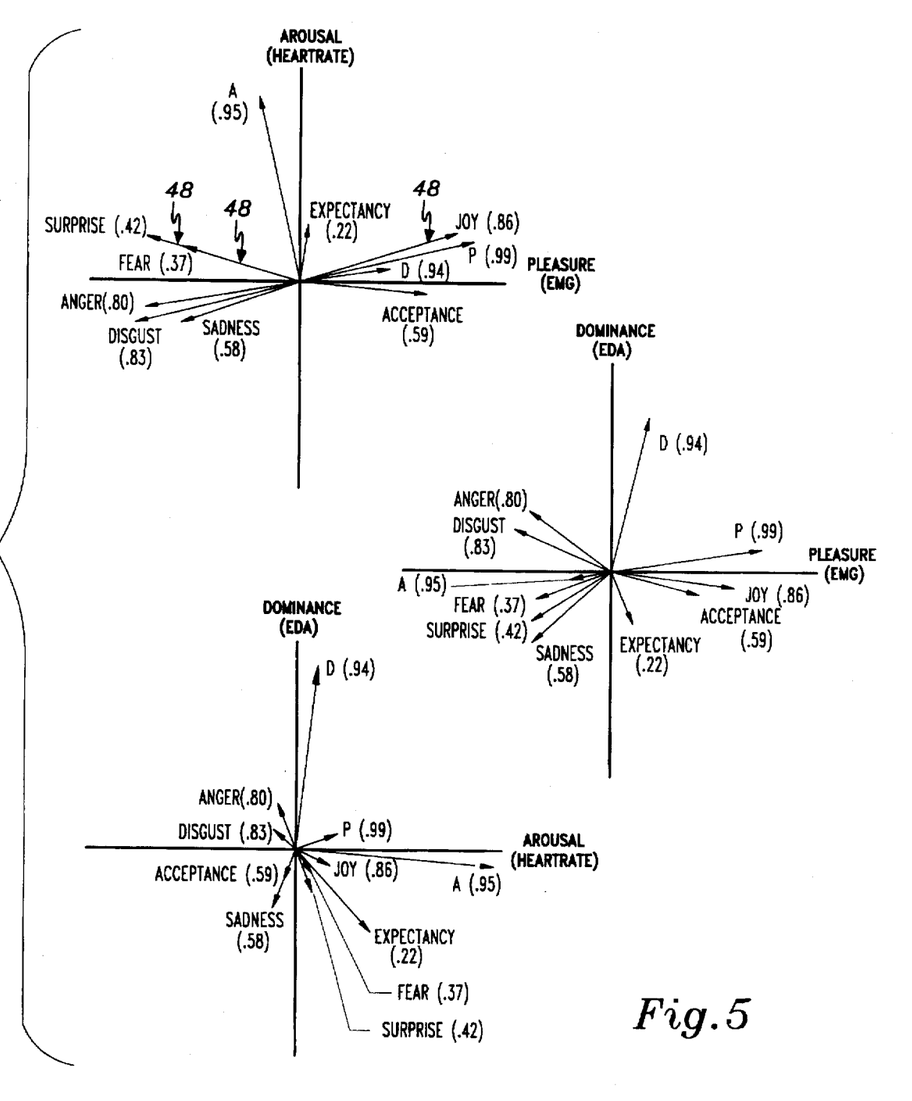
FIG. 5 is a diagrammatic representation of a three dimensional space and associated vectors for determining sector boundaries.

Based upon statistical calculations and accepted theory of emotional response, FIGS. 3, 4 and 5 illustrate the successive stages by which the program prepares the graphical representation of each of the three final interaction indices 51,53,55. Each final interaction index is based upon an interaction index 24 as shown in FIG. 3, which is a graphical representation of the area of all z-score point as plotted on two axes 29 having three uniglass intervals ranging from 3 to −3, based on the units of standard deviation as previously described for 100% of the population sample. Each interaction index 24 is divided into four labelled quadrants 41,43,43,44 by two axes intersecting at the origin, each successive axis being labelled for each different one of a pair of physiological variables being measured for all possible pair combinations. Therefore three interaction indices may be expressed for each of the physiological variables measured: EMG and heartrate 25, EMG and EDA 26 and EDA and heartrate 27.

Next the program again uses accepted psychological theory to associate each axis with a construction wherein a sate of feeling is expressed on a bipolar continuum or scale. Thus a bipolar dimension for a state of feeling can be superimposed upon a physiological axis. Again as shown in FIG. 4, the interaction index 25 has an axis for EMG 50, EMG being the electrical activity measured in muscles, being associated with the dimension of pleasure. In practice of the theory relied upon, it has been shown at muscles involved in positive and negative facial expressions, such as smiles, laughter, and frowns can be measured to accurately predict the dimensional extremes of pleasure. By plotting the z-score associated with EMG, a corresponding bipolar adjective, such as (pleasure-displeasure) can be associated with the dimension of Pleasure. Other bipolar adjectives which can be associated with the remaining dimensions of the preferred embodiment may include, for the Arousal dimension (operationalized by heartrate), "aroused-unaroused" or "frantic excitement-sleep", and, for the Dominance dimension (operationalized by EDA), "dominant-submissive".

Thus, as shown in the preferred embodiment, the three interaction indices 25,26.27 may be expressed not only for each of the physiological variables measured, but for each dimension being superimposed on each associated axis: Arousal(Heartrate)Pleasure(EMG) 25, Dominance(EDA)-Pleasure(EMG) 26 and Dominance(EDA)-Arousal (Heartrate) 27.

Next, eight sectors 34 are superimposed on the area comprising the graph, each sector 34 representing a different one of eight basic states of feeling, as adjectivally described, which can be correlated to the dimensional space of each interaction index. A model expanded into more than the eight basic states by adding more emotional states can obviously be created by adding more labelled sectors.

The software program subdivides the four quadrants 41,42,43,44 into sectors, as shown in FIG. 4, having boundaries between each of eight basic sectors 34. The eight basic sectors are labelled surprise 36, fear 37, anger 38, disgust 39, sadness 40, acceptance 45, joy 46, and expectancy 47. Referring now to FIG. 5, sector boundaries 60 between each of the eight sectors 34 are established by the software program to include a predetermined angle associated with each of a plurality of vectors 48 for each of the eight states of feeling placed in a three-dimensional emotion space (as determined by a study by Havelena and Holbrook (1986) using a regression analysis). On this basis, the angle of each vector 48 is transferred onto the graph area of the present invention in a two-dimensional space to form the appropriate sector boundary 60 associated with each such vector. Hence, the resulting index can be represented showing the quadrants subdivided into sectors on each of the three interaction indices 24 as shown in FIG. 3 as sectored interaction indices 25,26,27.

Figure 6A:
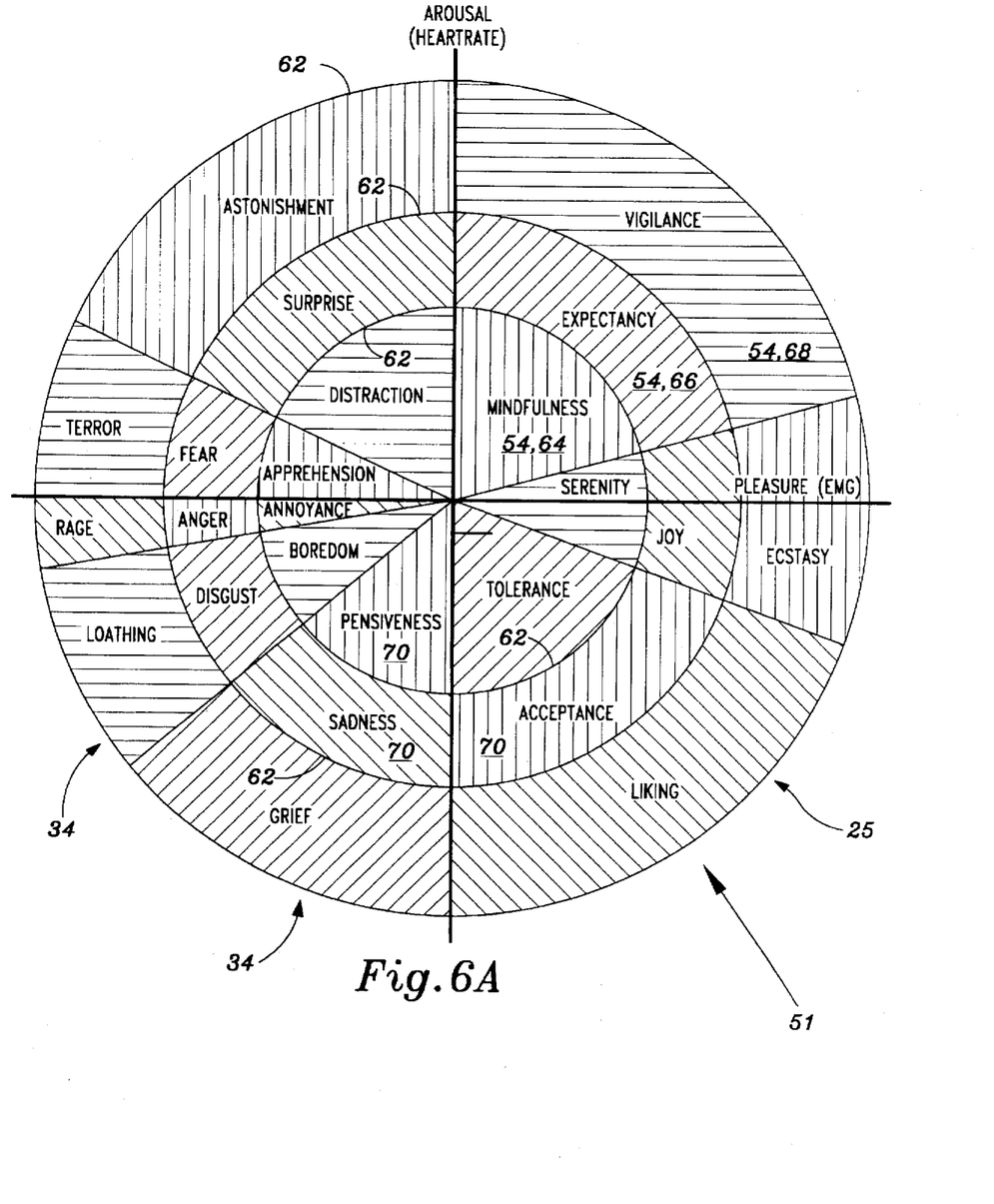
FIGS. 6A, 6B and 6C are a diagrammatic representations of three final interaction indices as displayed in the screen format as shown in FIG. 2 generated by a graphics and statistical program.
Figure 6B:
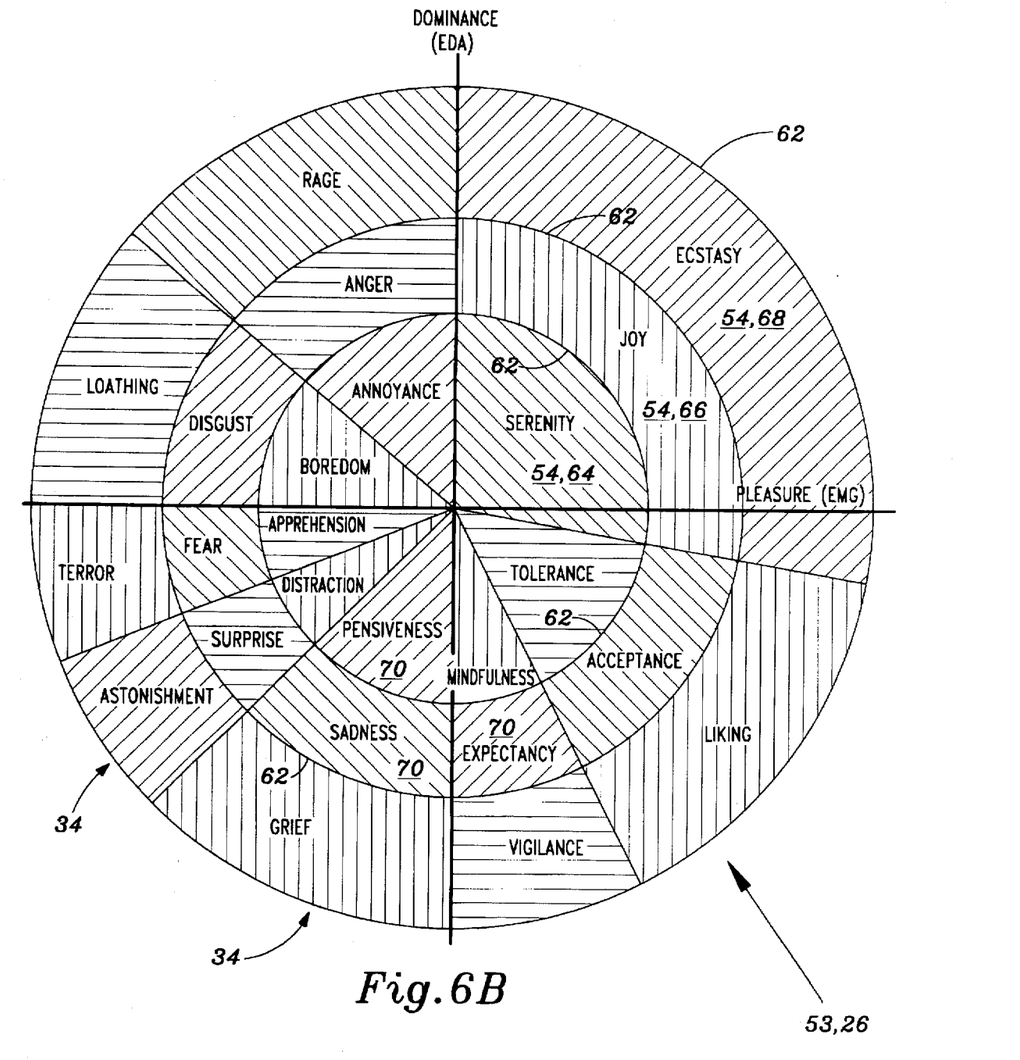
Figure 6C:
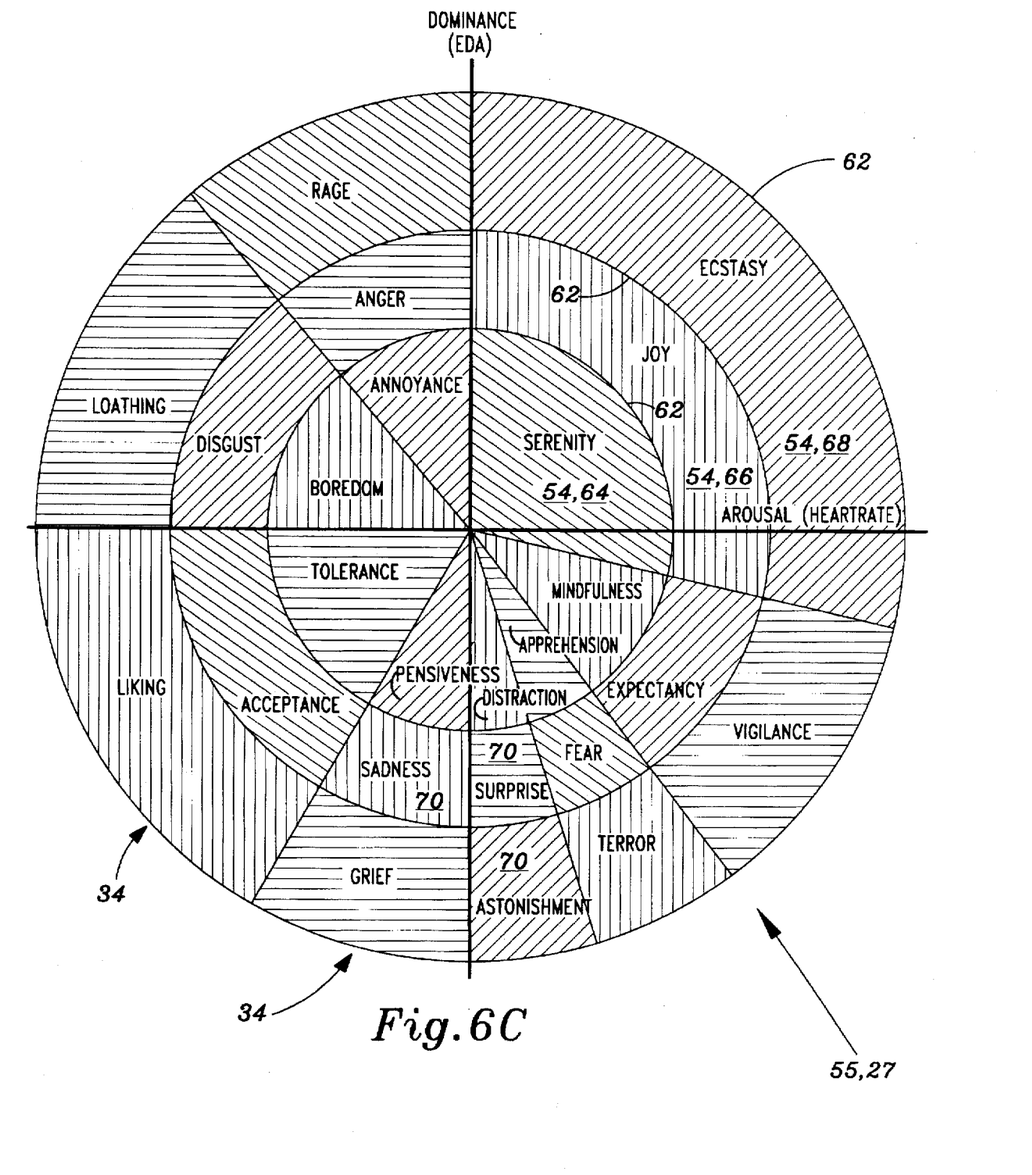

Turning now to FIGS. 6A, 6B, and 6C, each sectored interaction index is shown having intensity boundaries 62 and intensity bands 54 for each of the eight emotions overlaid upon the eight sectors 34. FIG. 6A represents a final interaction index 51, as also generally shown in FIG. 2, having intensity bands 54 overlaid upon sectored interaction index 25. FIG. 6B represents a final interaction index 53, as also generally shown in FIG. 2, having intensity bands 54 overlaid upon sectored interaction index 26. FIG. 6C represents a final interaction index 55, as also generally shown in FIG. 2, having intensity bands 54 overlaid upon sectored interaction index 27. Because each graph is a unitless dimension, an intensity boundary 62 for each of the eight feeling states or sectors 34 can be calculated and further superimposed upon each interaction index. Thus, superimposed on the space comprising the graph of each interaction index, 24 areas are provided having boundaries 62 between each area.

Each boundary is established by calculating a value of z (not to be confused with the z-score) from the below formula, at each one, two and three standard deviation intervals and scribing an arc radially from the origin of the interaction axes at the length of z. The program thus substitutes each the x and y coordinates of the standard deviation for each of the physiological variable intervals at positive and negative 1, 2, and 3 on the interaction index axes into the formula, $z^2=x^2+y^2$. The resulting value for z is the distance of the hypotenuse formed from the origin O of the interaction index axes along each axis to the intensity boundary 62.

The eight sectors 34 are thus each transformed into 3 bands 64,66,68 and 24 areas 70 having intensity descriptors associated with each band and area. The center band 66 is a mid-level of intensity, being associated with the descriptor for the state of feeling of the sector 34, and the inner band 64 and outer band 68 being a low and high level of intensity, respectively. Each of the bipolar adjectives associated with the intensities for that sector 34 are labelled accordingly, i.e., each area 70 bounded within each sector 34 is assigned a bipolar adjective associated with the high or low intensity of state of feeling.

Having thus created the final interaction indices 51,53,55, a z-score of any individual subject tested may then be plotted by the program as a point falling within a sector 34 or intensity area 70 and which point is automatically associated with the indicia for the state of feeling indicated for each sector or area. As shown in FIG. 2, the measured z-score is plotted on all possible pair combinations of the physiological variables, e.g. final interaction indices 51,53,55. Each of the plotted points at each time interval 28 are given time point identifying indicia 72 and graphed having connections between quadrants of a final interaction index, thus forming a non-linear trajectory 74 across each final interaction index. The screen displays the semantic descriptor 30 for each point falling on a sector 34 of the final interaction index.

Therefore, a plotted point falling within a sector and band area is automatically associated with the indicia describing the state and intensity of feeling indicated for each sector and tied in time to successive points by a graphical representation of trajectory. Thus, a researcher can obtain an immediate visual impression of both the momentary impact of a stimulus presented, and, see the emotional tendency and progression of an individual as the stimulus changes over time.

Figure 7:
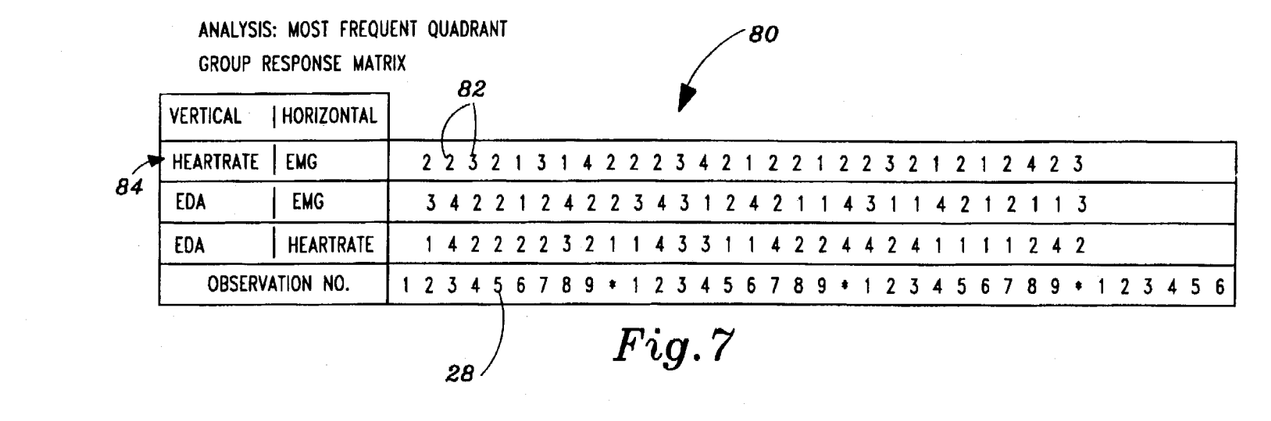
FIG. 7 is a diagrammatic representation of a Most Frequent Quadrant Group Response Matrix generated by a statistical program.

Finally, the program is further programmed to be capable to serve as a summary means for determining a group response, which statistically analyses the placement of each plotted point of each quadrant of each interaction index for a given time interval. As represented by the matrix 80 shown in FIG. 7, the software program associates each plotted z-score with each quadrant of each interaction index for each individual measured at a time interval or observation point, places each associated plotted z-score into a group characterized by a quadrant indicia 82 for each quadrant including a plotted z-score, calculates the most frequently appearing quadrant by comparing the number of said z-scores included in each said group and identifies a most frequently appearing by its quadrant indicia 82. The software program is capable of generating the matrix 80 wherein each said quadrant indicia is appropriately placed onto said matrix comprising of at least one column and at least one row for identifying the physiological variables measured 84 and the time interval 28 for display upon said interactive multimedia computer system 10.

Figure 8:
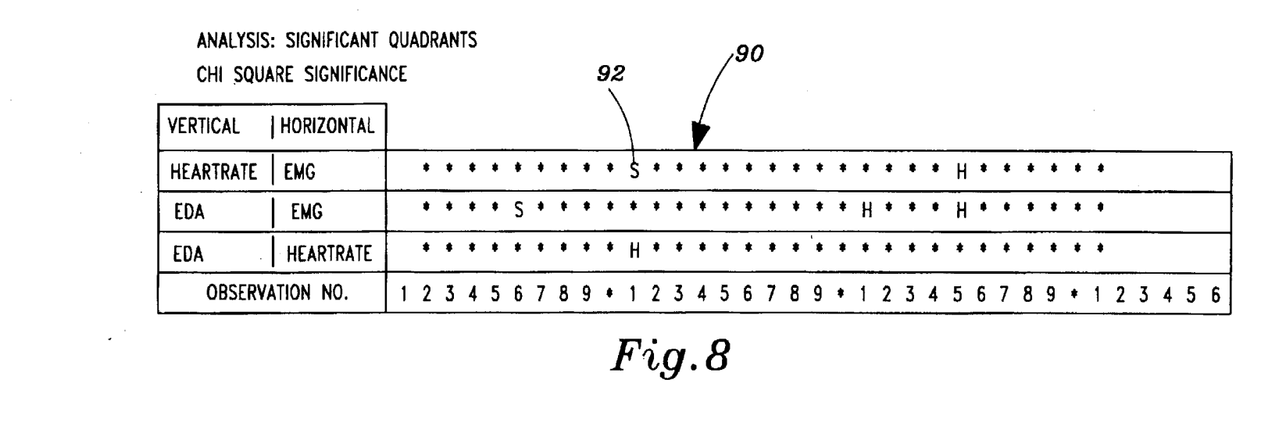
FIG. 8 is a diagrammatic representation of a chi-square significance statistical analysis matrix associated with the Most Frequent Quadrant Group Response Matrix shown in FIG. 7.

As shown in FIG. 2 and FIG. 8, an alternative statistical matrix 90 is displayed for a chi-square analysis. The software is further capable of performing a chi-square analysis for statistical significance by calculating the appropriate statistical formulas using the appearance of each quadrant number at a given time point as a variable and thereupon superimpose resulting indicia of significance 92 onto the matrix 90.

A second of embodiment of the present invention 1 incorporates the use of an eye movement detector or occulometer for determining a viewing point on the stimulus 25 by at least one eye of an individual. Occulometers are known in the art and any type suitable for use with the present invention may be chosen for use with the invention. The informational data output from an eye movement detector can be obtained from a viewing chamber wherein a subjects head is fixed in a stationary position by means of straps, clamps or a bite bar. Thus, an occulometer can be used to determine the exact eye movement pattern of the eye, and hence the exact location of fixation of the eye on a target stimulus can be determined from such shape. The output is recorded and used as input into the software program of the present invention 10.

The software program compares the time interval 28 and view point of the eye on the stimulus 25 in a similar manner described above for coordinating the time interval with each physiological measurement. The program may then add indicia indicating the position of the viewpoint on the stimulus 25 as shown in the graphical display screen 11, whereby the researcher can further enrich the interpretation of the results by observing the change of position from stimulus to stimulus over time, thus recognizing an eye movement pattern.

It is to be understood that the present invention is not limited to the sole embodiment described above, but encompasses any and all embodiments within the scope of the following claims.

I claim:

1. A multimedia computerized system for measuring, analyzing, storing and displaying emotional responses elicited by one or more human beings being or having been presented a stimulus, comprising:

stimulus presentation means for presenting a stimulus occurring over a predetermined period of time to each of one or more individuals forming a population sample;

measuring means for measuring and recording a plurality of values for each of a plurality of physiological variables associated with said each of one or more individuals, said measuring means adapted to record said value at each of a plurality of preselected time intervals over said predetermined period of time during which said stimulus is presented, said measuring means further adapted to output said value at said preselected intervals of time;

translation means for receiving and translating each said value by statistical calculation into a unitless statistical measure known as a z-score, wherein said translation means includes a statistical and graphics software program and a computer processing means having a memory on which said software program is installed and operationally linked to said measuring means and programmed to receive said output value as input, wherein further said program is capable of at least generating a plurality of interaction indices, each index comprising two axes and four quadrants defined by said two axes, each quadrant being labelled by quadrant indicia, each axis associated with a different one of a pair of said plurality of physiological variables and all possible pair combinations of said physiological variables being represented among said plurality of interaction indices, wherein further a plurality of sectors are superimposed on the area comprising each interaction index wherein a semantic descriptor identifying a basic state of human feeling labels each said sector, wherein further said program is capable of plotting at least one of each said z-score generated on said interaction index and placing an associated time interval identifying indicia on a plotted z-score whereby a labelled trajectory across each interaction index is formed and whereby further a semantic descriptor is automatically applied to each z-score falling on said sector of said interaction index; and, interactive multimedia computerized means for electronically storing, displaying and retrieving information and capable of at least visually displaying at least one said stimulus presented at a said time interval, at least one semantic descriptor associated with said at least one said stimulus presented, and said interaction index associated with said at least one semantic descriptor associated with said at least one stimulus presented.

2. The system according to claim 1, further including summary means for determining a group response wherein said software program associates each plotted z-score with each said quadrant of each interaction index for each individual measured at a said time point, places each said associated plotted z-score into a group characterized by a quadrant indicia for each said quadrant including a plotted z-score, calculates the most frequently appearing quadrant by comparing said numbers of said z-scores included in each said group and identifies a most frequently appearing by its quadrant indicia, wherein further said software program is capable of generating a matrix wherein each said quadrant indicia is appropriately placed onto said matrix comprising of at least one column and at least one row for identifying said physiological variable measured and said time interval for display upon said interactive multimedia computerized means.

3. The system according to claim 2, wherein said program is capable of performing a chi-square analysis for statistical significance of appearance of each said quadrant indicia at a given time point, and substitute resulting indicia of significance onto said matrix.

4. The system according to claim 1, wherein said interactive multimedia computerized means is further programmed and capable of at least visually displaying said matrix of physiological variables measured at the selected time interval.

5. The system according to claim 1, wherein said interactive multimedia computerized means is programmed to display a scroll bar for interactive use by a user to retrieve any one said time interval and associated visual display.

6. The system according to claim 1, wherein each said sector is further subdivided into a plurality of concentric bands having a boundary line between each band, each of said plurality of bands having an intensity descriptor labelling each band, whereby at least 24 labelled areas are provided.

7. The system according to claim 1, wherein said translating program is further capable of calculating said boundaries of said concentric band for each of said eight sectors by substituting each the x and y coordinates of a standard deviation for the z-score plotted on the interaction index axes into the formula, $z^2 = x^2 y^2$, and obtaining a resulting value for z and taking z as the distance from the origin of the interaction index axes to each boundary.

8. The system according to claim 1, wherein said semantic descriptor identifying a basic state of human feeling for labelling each said sector is selected from the group consisting of surprise, fear, anger, disgust, sadness, acceptance, joy, and expectancy.

9. The system according to claim 8, wherein each said sector is further subdivided into a plurality of concentric bands having a boundary line between each band, each of said plurality of bands having an intensity descriptor labelling each band, whereby at least 24 labelled areas are provided, and said semantic descriptors are positioned within a center band representing a mid-level of intensity associated with an intensity descriptor for the state of feeling of said sector, an inner band representing a low-level of intensity associated with an intensity descriptor and an outer band representing a low-level of intensity associated with an intensity descriptor.

10. The system according to claim 1, wherein each said axis is divided into three unitless increments from its origin in a positive and negative direction.

11. The system according to claim 1, wherein said software is programmed to define the position of each said sector on said interaction index by calculating an angle associated with each of a plurality of vectors for each of a plurality of states of feeling placed in a three-dimensional emotion space and to transfer said angle onto each sector to form the appropriate boundary for each such vector.

12. The system according to claim 11, wherein each said axis has an indicia associated with one of said measuring means and further has superimposed on each axis a dimension associated with a human state of feeling corresponding to one of each said measuring means, wherein an associated measuring means-dimension indicia is selected from the group of heartrate-arousal, electrodermal activity dominance, and electromyograph-pleasure.

13. The system according to claim 1, wherein each of said measuring means is selected from the group consisting of electromyograph, heartrate monitor, galvanic skin response monitor, skin conductance response monitor, and skin potential response monitor.

14. The system according to claim 1, wherein said measuring means is operably linked to said stimulus presentation device by a signaling means which starts recording of said measuring means at the moment said stimulus is presented.

15. A multimedia computerized system for measuring, analyzing, storing and displaying emotional responses elicited by one or more human beings being or having been presented a stimulus, comprising:

stimulus presentation means for presenting a stimulus occurring over a predetermined period of time to each of one or more individuals forming a population sample;

an eye movement detector for determining a viewing point on said stimulus by at least one eye of each of said one or more individuals;

measuring means for measuring and recording a plurality of values for each of a plurality of physiological variables associated with said each of one or more individuals, said measuring means adapted to record said value at each of a plurality of preselected time intervals over said predetermined period of time during which said stimulus is presented, said measuring means further adapted to output said value at said preselected intervals of time;

translation means for receiving and translating each said value by statistical calculation into a unitless statistical measure known as a z-score, wherein said translation means includes a statistical and graphics software program and a computer processing means having a memory on which said software program is installed and operationally linked to said measuring means and said eye movement detector and programmed to receive said output value from said measuring means as input and to coordinate output data from said eye movement detector with said output value at same said time interval, wherein further said program is capable of at least generating a plurality of interaction indices, each index comprising two axes and four quadrants defined by said two axes, each quadrant being labelled by quadrant indicia, each axis associated with a different one of a pair of said plurality of physiological variables and all possible pair combinations of said physiological variables being represented among said plurality of interaction indices, wherein further a plurality of sectors are superimposed on the area comprising each interaction index wherein a semantic descriptor identifying a basic state of human feeling labels each said sector, wherein further said program is capable of plotting at least one of each said z-score generated on said interaction index and placing an associated time interval identifying indicia on a plotted z-score whereby a labelled trajectory across each interaction index is formed and whereby further a semantic descriptor is automatically applied to each z-score falling on said sector of said interaction index; and, interactive multimedia computerized means for electronically storing, displaying and retrieving information and capable of at least visually displaying at least one said stimulus presented at a said time interval, said view point as detected by said eye movement detector, at least one semantic descriptor associated with said at least one said stimulus presented, and said interaction index associated with said at least one semantic descriptor associated with said at least one stimulus presented.

* * * * *